United States Patent
Gardiner

(10) Patent No.: US 6,390,814 B1
(45) Date of Patent: May 21, 2002

(54) ENDODONTIC APPLIANCE WHICH STOPS INSTRUMENTS FROM EXTENDING TOO FAR INTO A ROOT CANAL DURING TREATMENT

(76) Inventor: Vernon Gardiner, 90 Barnett Street, Montego-bay (JM)

(*) Notice: Subject to any disclaimer, the term of this patent is extended or adjusted under 35 U.S.C. 154(b) by 0 days.

(21) Appl. No.: 09/642,507

(22) Filed: Aug. 18, 2000

Related U.S. Application Data

(60) Provisional application No. 60/149,363, filed on Aug. 18, 1999.

(51) Int. Cl.[7] .................................................. A61C 3/00
(52) U.S. Cl. .......................................... 433/75; 433/102
(58) Field of Search .............................. 433/39, 75, 76, 433/102, 72

(56) References Cited

U.S. PATENT DOCUMENTS

| | | | |
|---|---|---|---|
| 1,407,840 A | * 2/1922 | Cruttenden | 433/76 |
| 1,943,668 A | * 1/1934 | Hartman | 433/75 |
| 3,295,208 A | 1/1967 | Redtenbacher | |
| 3,781,996 A | 1/1974 | Saffro | |
| 3,838,517 A | 10/1974 | Michnick | |
| 3,961,422 A | 6/1976 | Riitano | |
| 4,028,810 A | 6/1977 | Vice | |
| 4,165,562 A | 8/1979 | Sarfatti | |
| 4,177,565 A | * 12/1979 | Heasley | 433/75 |
| 4,571,183 A | 2/1986 | Nash | 433/116 |
| 4,639,221 A | 1/1987 | Sairenji | 433/139 |
| 4,787,849 A | 11/1988 | Jacoby et al. | 433/139 |
| 5,295,833 A | 3/1994 | Chihiro et al. | 433/224 |
| RE35,147 E | 1/1996 | Apap et al. | 433/102 |
| 5,807,106 A | 9/1998 | Heath | 433/102 |
| 5,888,065 A | * 3/1999 | Sussman | 433/76 |
| 5,915,964 A | 6/1999 | Walia | 433/102 |
| 6,062,856 A | * 5/2000 | Sussman | 433/76 |

* cited by examiner

Primary Examiner—Cary E. O'Connor
(74) Attorney, Agent, or Firm—Brown & Michaels, PC

(57) ABSTRACT

The appliance of the present invention works effectively during root canal treatment by being firmly attached to the tooth to be treated and having a fixed platform from which the file can have a fixed working length. The appliance has three functional parts: (1) an attachment section that is held against the tooth by a matrix retainer and band, (2) a resting section that rests against the occlusal or top of the crown of the tooth, and (3) a guide section with a hole that pivots or is fixed over the tooth. The appliance is preferably attached to the tooth by any tofflemiere type matrix holder and band. Once the working or desired length of the file is obtained, then it is placed into the guide section of the appliance which is stationary in one plane. Therefore, the file cannot extend further than the desired length into the canal. This appliance provides an effective stop for the file while it is being used.

21 Claims, 9 Drawing Sheets

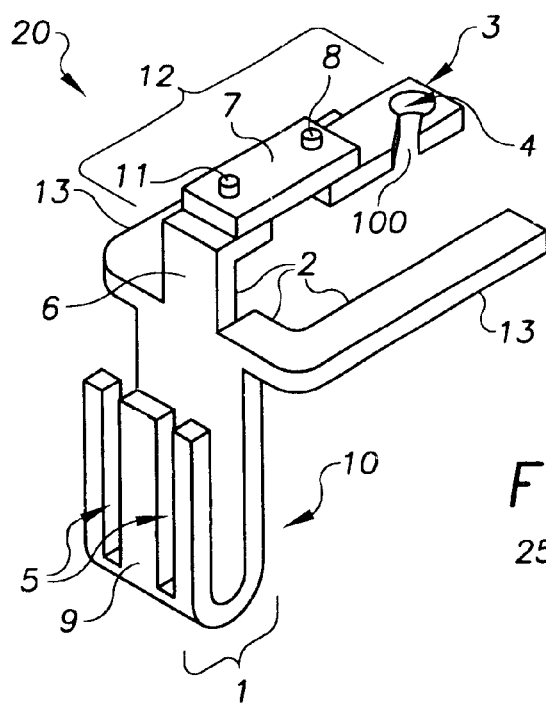
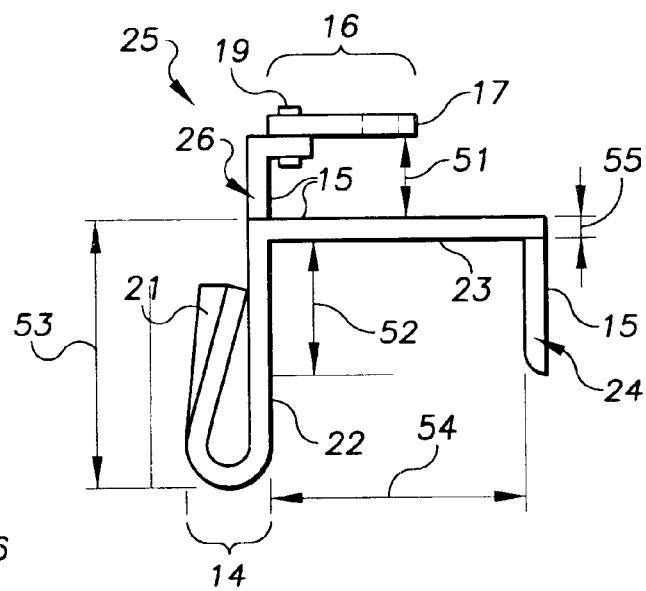
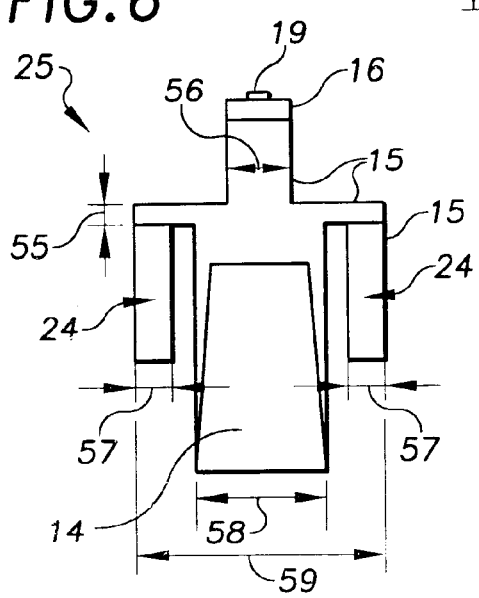

ENDODONTIC APPLIANCE WHICH STOPS INSTRUMENTS FROM EXTENDING TOO FAR INTO A ROOT CANAL DURING TREATMENT

REFERENCE TO RELATED APPLICATIONS

This application claims an invention which was disclosed in Provisional Application No. 60/149,363, filed Aug. 18, 1999, entitled "APPLIANCE THAT WILL HOLD WHILE THEY ARE BEING USED, THE INSTRUMENTS USED IN ROOT CANAL TREATMENT HENCE STOPPING THEM FROM GOING TOO FAR INTO THE CANAL DURING THE PROCEDURE". The benefit under 35 USC §119(e) of the United States provisional application is hereby claimed, and the aforementioned application is hereby incorporated herein by reference.

BACKGROUND OF THE INVENTION

1. Field of the Invention

The invention pertains to the field of dental instruments. More particularly, the invention pertains to appliances which keep files and/or reamers from progressing too far into a root canal during treatment.

2. Description of Related Art

When a tooth experiences trauma including infection or a nerve in the root being adversely affected by proximity to a deeply set filling, the body (dental pulp) takes defensive measures to constrict the root canal to isolate it, or its defenses may be overcome by the irritant. If the diagnostic tests of the tooth reveal irreversible damage, a root canal or endodontic procedure is needed. A root canal treatment entails the removal of the central soft portion (nerves, blood vessels, tissues etc.) of the tooth. The empty space or canal is then filled with an inert material. The canal is sometimes too narrow and/or infected to effectively place the inert material inside it. Instruments, usually files and/or reamers, herein collectively termed "files", are used to clean and/or widen this canal. Their mode of action while being used is either a push-pull or twisting motion.

In cleaning out the canal, it is important that the clinician not change the general shape of the canal, for example, by creating a ledge in it or by changing its curvature since if either of these events occur, there is an increased probability that one of the successively larger and stiffer files used to clean the canal will perforate the root wall. This in most cases requires surgical correction or extraction of the tooth. This complicates and prolongs the treatment, causing discomfort to patients.

In the preparation of root canals, it is the present practice to enter the chamber of the tooth with a file to enlarge the root canal. A plurality of endodontic files of increasing diameter are employed to enlarge the root canal to create a channel of size that can practically be filled with a medicament and then sealed. It is important in the preparation of the root canal to control the length of the file in order to limit the depth of penetration to avoid injury. The desired depth is called the working length.

The length of the tooth involved, as well as the length of the root canal, is determined by means of X-rays, and various techniques and devices have been devised in the past for limiting the depth of penetration of the root canal files to the root tip. Thus, many dentists employ a stop member which is penetrated by the root canal file for the desired distance, with the stop member being positioned to engage the top of the tooth to limit penetration.

However, these stop members, which are generally rubber stoppers, are easily displaced, particularly in working within the limited area of a patient's mouth and considering the relatively small size of the instruments involved. There is nothing to stop the files from going too far into the canal.

It is difficult for the endodontist to precisely judge when the file has reached the end of the tooth. Additionally, the rubber stopper is both flexible and movable and can therefore allow the file to proceed deeper into the root canal then may be actually desired. In other instances, the inadequacies of the equipment result in incomplete penetration. Either too great or too shallow depth penetration could cause failure of the entire procedure. An additional problem is presented in that each individual file and its rubber stopper must be separately gauged against a separate scale or ruler and then individually set to the depth indicated in the x-ray. This procedure can involve inherent inaccuracies and a great deal of time and inconvenience to the dentist. Inaccuracies can also occur because of the number of manual operations involved. Further, problems relating to contamination of the file during this measurement or gauging procedure are likely to occur.

During an endodontic procedure, accuracy is compromised in both the determination of the working length, and maintaining this working length. In determining the working length, measuring any length requires two points. The first point that a dental practitioner uses is the tooth apex. The second is however an arbitrary point on the tooth that is lined up with a rubber stopper. Most times there is no clear reference point on the tooth that can be used repeatedly to get the same correct length. Either a different point is used or it is viewed at a different angle to get another measurement. It is very difficult to remember the reference points for each canal in multi-canal procedures. Some in the field say that practice and experience allows them to work around this problem. However, in reality, accuracy is not in the eye of the beholder.

When attempting to maintain the working length, assuming the accuracy of this length based on only one fixed point, the files are not effectively stopped from going too far into the canal. The point(s) chosen is not a platform that can support anything. The rubber stoppers do not provide any support if pressure is applied. During filing, the rubber stops give in a millimeter or two. Since in root canal treatment dentists generally go into the half-mm range, this reduces the accuracy of the whole procedure. A common defense to this problem is that the apical constriction stops the file. However, if this were the case, then there would be no reason to determine the length in the first place. Why not simply go ahead and file without finding the working length? In essence, this is currently what is being done since a working length is being determined and then can not be maintained.

It is almost impossible to move an unsupported object manually in one plane and keep it fixed in another plane. This principle is what root canal treatment has been based or more accurately not based upon for decades. Radiographs along with sophisticated and expensive instruments are used to determine the working length of the tooth. This length is indicated on the file. There is, however, no way to stop the file from overextending in the canal while it is being used.

Several prior art patents have tried to solve these problems.

U.S. Pat. No. 3,781,996, "ROOT CANAL REVERSIBLE STOP," Saffro (1974), shows an endodontic file with an intermediate part between a cutting portion and a handle which contains a series of reversible stop members. The fact that the stop is found on the instrument means that the point of measurement or reference changes with the movement or shifting of the instrument, hence it is impossible to get the same measurement twice. Since the essence of root canal treatment is to transfer measurement all the time, this system is not very accurate.

U.S. Pat. No. 3,838,517, "COMBINATION DEPTH STOP AND GAUGE ASSEMBLY FOR A DENTAL DRILL", Michnick (1974), is an assembly which attaches to a dental drill. The assembly includes a surface which controls the depth of the cut by the drill. The drill bit runs through this surface, and acts as a depth stop for the drill. The surface controls the depth of a cut, but the invention is not interested in working length, nor is it used for files. This mechanical and electrical device has stops that project between the device and the tooth limiting the extent to which the drill or instrument goes into the tooth. These stops work only with mechanical or electrical devices. They cannot currently be used for manual manipulation of the root canal since the stops are an integral part of the assembly of the device.

U.S. Pat. No. 3,961,422, "STOP DEVICE FOR ENDODONTIC INSTRUMENTS," Riitano et al. (1976), shows a stop for limiting the depth of penetration of an elongated dental instrument usable in an endodontic procedure. The stop is in the form of a disc divided into two halves. Manually assembling the two halves requires that they are big enough to handle with the fingers. If they were this big, then the assembled disc would be bulky and too large to work with in the confines of the mouth.

U.S. Pat. No. 4,028,810, "ROOT CANAL FILE," Vice (1977), is an endodontic instrument for treating a pulp canal which includes a handle portion adjustably mounted in telescoping relation on the shaft of an elongated working tool, with cooperating grooves in the shaft and handle preventing relative movement during use of the instrument. The working length of the tool projecting from the handle is adjusted and the tool and handle are interlocked. The end of the handle acts as a positive stop limiting the depth of penetration of the working tool portion during use of the instrument. The main disadvantage of this device is that it is tedious to change or adjust the stops since special tools are needed to do so. The fact that the stop is found on the instrument means that the point of measurement or reference changes with the movement or shifting of the instrument, hence it is impossible to get the same measurement twice. Since the essence of root canal treatment is to transfer measurement all the time, this system is not very accurate.

U.S. Pat. No. 4,165,562, "PRECISION ENDODONTIC FILE," Sarfatti (1979) discloses an endodontic file with a threaded base and a threaded sleeve. The threaded sleeve receives the threaded base to facilitate adjustment of the file. The fact that the stop is found on the instrument means that the point of measurement or reference changes with the movement or shifting of the instrument, hence it is impossible to get the same measurement twice. Since the essence of root canal treatment is to transfer measurement all the time, this system is not very accurate.

U.S. Pat. No. 4,571,183, "VIBRATORY ENDODONTIC DEVICE," Nash (1986), describes a vibratory endodontic device for mechanical preparation of dental radicular canals such as root canals, prior to their obturation. The device includes an endodontic file connected to a drive means for vibratory movement. This mechanical and electrical device has stops that project between the device and the tooth limiting the extent to which the drill or instrument goes into the tooth. These stops work only with mechanical or electrical devices. They cannot currently be used for manual manipulation of the root canal since the stops are an integral part of the assembly of the device.

U.S. Pat. No. 5,295,833, "DENTAL ROOT CANAL DIAGNOSTIC AND TREATING EQUIPMENT," Chihiro (1994), teaches dental root canal diagnostic and treating equipment with specific positions, which serve as the reference positions. One of the reference positions to be set is the working length. This device electronically tells a dentist when the tip of the instrument reaches the tip of the root canal. It however does not or cannot transfer that measurement because it has no fixed precise location near the crown with which to repeat the measurement over and over again from the same points of reference.

U.S. Pat. No. RE35,147, "DENTAL TOOL HOLDER," Apap et al. (1996), shows a dental tool holder for an endodontic filing tool in which the shaft of the worktool is held so as to be secured against rotational and axial movements. The worktool is set in motion with an exciter device having a component which is transverse relative to the axis of the worktool. A stop is guided in the housing of the handpiece with a rod containing teeth. This mechanical and electrical device has stops that project between the device and the tooth limiting the extent to which the drill or instrument goes into the tooth. These stops work only with mechanical or electrical devices. They cannot currently be used for manual manipulation of the root canal since the stops are an integral part of the assembly of the device.

U.S. Pat. No. 5,807,106 "ENDODONTIC INSTRUMENT HAVING DEPTH CALIBRATIONS AND METHOD OF FABRICATING SAME," Heath (1998), discloses a method of fabricating an endodontic instrument with depth indicating calibrations formed between the handle and the fluted tapered end portion. The calibrations are formed by a cold rolling operation. The device has no effective stop, but the grooves on the instrument will show up on the x-ray when the working length is being determined.

U.S. Pat. No. 5,915,964, "FLEXIBLE GUIDED FILE FOR ROOT CANAL PROCEDURES," Walia (1999), uses a noncutting file guide at the tip of a flexible file. The guide is first inserted into the root canal, and the file is then moved along the guide. This patent states that the instrument should be inserted until it stops at the tip of the root but if this could be done with certainty then a file or reamer could be used to do this in the first place since this would be a natural stop. If the ball at the end of the instrument is small and passes through the root opening at the tip then there is nothing to stop the whole apparatus from passing through if there is no effective stop at the crown portion of the tooth.

Errors in depth penetration of the file into the root canal, either too deep or too shallow, are the major cause of failure in endodontic procedures. In seeking to overcome such failure, the prior art endodontic instruments have been largely unsuccessful because of complexity or impracticability. Further, none of the devices currently available offer any assurity of maintaining sterility. The stops on the mechanical devices cannot be used without the device themselves or with other mechanical devices or with manual manipulation. The devices that use screw-on stops need specialized files. Specialized stops are needed for many of the prior art devices. All of the devices with the stops on the instruments themselves rely on an arbitrary point of reference on the tooth that vary depending on the line of sight.

Therefore, there is a need in the art for improved accuracy of the root canal procedure. Specifically, a fixed platform from which to measure and maintain the working length is needed.

SUMMARY OF THE INVENTION

The appliance of the present invention works effectively during root canal treatment by being firmly attached to the tooth to be treated and having a fixed platform from which the file can have a fixed working length. The appliance has three functional parts: (1) an attachment section that is held against the tooth by a matrix retainer and band, (2) a resting section that rests against the occlusal or top of the crown of the tooth, and (3) a guide section with a hole that pivots or is fixed over the tooth. The appliance is preferably attached to the tooth by any tofflemiere type matrix holder and band. Once the working or desired length of the file is obtained, then it is placed into the guide section of the appliance which is stationary in one plane. Therefore, the file cannot extend further than the desired length into the canal. This appliance provides an effective stop for the file while it is being used.

BRIEF DESCRIPTION OF THE DRAWINGS

FIG. 4 shows an isometric view of one embodiment of the appliance of the present invention.

FIG. 5 shows a side view of a second embodiment of the appliance of the present invention.

FIG. 6 shows a front view of a second embodiment of the appliance of the present invention.

DETAILED DESCRIPTION OF THE INVENTION

Figure 1:
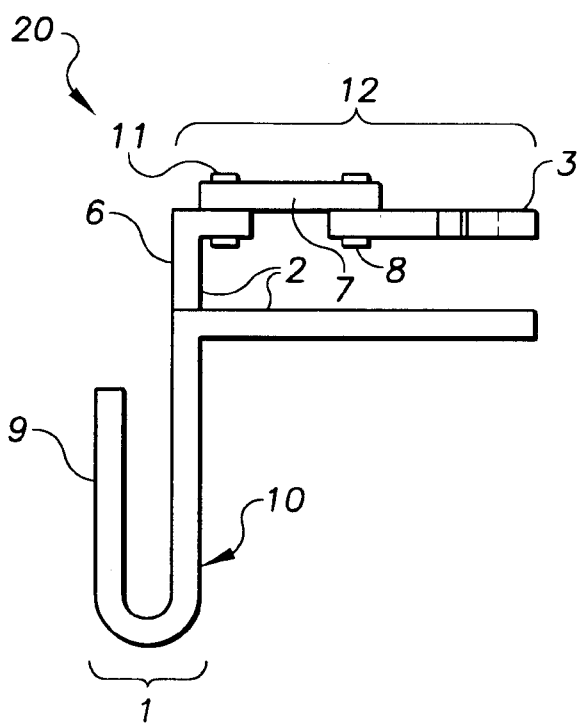
FIG. 1 shows a side view of one embodiment of the appliance of the present invention.
Figure 2:
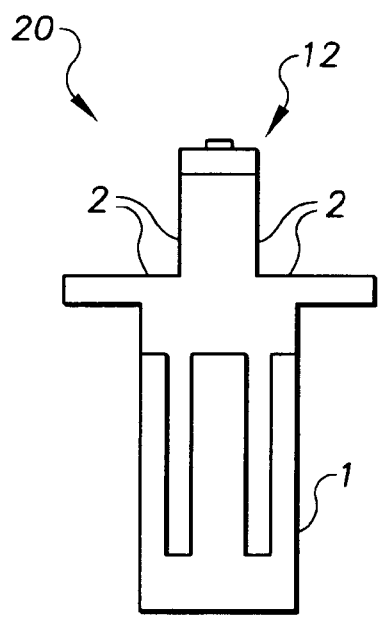
FIG. 2 shows a front view of one embodiment of the appliance of the present invention.

This appliance provides a stable, fixed platform on which to measure and use the root canal treatment instruments. These instruments have a hard stopper that abuts against this platform. The platform is able to move horizontally (in the case of molars) while still maintaining the integrity of the vertical dimension.

As discussed below, the appliance of the present invention has three functional parts: (1) a section that is held against the tooth by a matrix retainer and band, (2) a section that rests against the occlusal or top of the crown of the tooth, and (3) a section with a hole that pivots or is fixed over the tooth.

The appliance functions like a rubber dam clamp. The buccal (cheek) section replaces the buccal wing of the clamp and the lingual (tongue) section functions as the lingual wing of the clamp. The section over the tooth in the center has an arm that swings to cover the occlusal area of the tooth. This applies mainly to molars.

The appliance is held firmly by the band against the tooth to stop any side to side movement. To aid in this restriction, the section that rests on the crown stops any vertical and to some extent lateral movement when the appliance is being used. A guide section, which either pivots or is fixed, holds the files while they are being used. The file abuts against this guide section and the file is stopped from going too far into the canal. Since the guide section covers the crown of the tooth, whichever canal needs to be accessed can be done through the hole in the arm.

The appliance is composed preferably of a thin metal. In order for the appliance to be durable, a strong non-corrosive metal or metal alloy is preferably used. An example of this type of metal is stainless steel. Alternatively, the appliance could be made of a transparent, clear hard plastic. If the appliance is made of plastic, it can be disposable.

The appliance is preferably bent or molded into the required shape from a single sheet of material. The appliance is preferably approximately 1 mm thick.

Referring to FIGS. 1–4, in one embodiment there are three pieces of the appliance (20) to manufacture. All of these pieces are preferably cut or formed from a single sheet of material. Alternatively, they are manufactured separately. The first, largest piece includes an attachment section (1) and a resting section (2). Once this piece is initially formed, only two grooves (5) and one hole need to be placed in this piece of the material. Two additional pieces, elongated sections (3) and (7), make up the guide section (12), and are preferably also cut or formed from the material. Two holes preferably need to be placed in each of these elongated sections (3) and (7). The two elongated sections (3) and (7) are connected through one pair of holes and one free end is connected to the elevated central portion (6) of the resting section (2) (see FIG. 3) of the major piece of the appliance (20). These elongated sections (3) and (7) are connected at one end to allow the other end of elongated section (3), which is free, to move to cover all the area enclosed within the arms (13) of the resting section (2).

The appliance (20) includes the attachment section (1), which fixes the appliance in the mouth to the tooth by utilizing a dental matrix holder and band. Branching from an arm (10) of the attachment section (1) in a plane perpendicular to the arm (10) are two arms (13) of the resting section (2). These arms (13) rest on the tooth being operated on or adjacent teeth during use. The guide section (12) holds and supports the file in a fixed horizontal plane that is perpendicular to the axis of the files.

The attachment section (1) utilizes a matrix retainer and band, and is preferably U-shaped in cross section (see FIG. 1) with the free end (9) having two grooves (5) running the length of it. The grooves (5) are used to facilitate the insertion of the matrix band that holds the appliance to the tooth during use. An arm (10) of the attachment section (1) is a continuation of the rest of the appliance (20).

Figure 3:
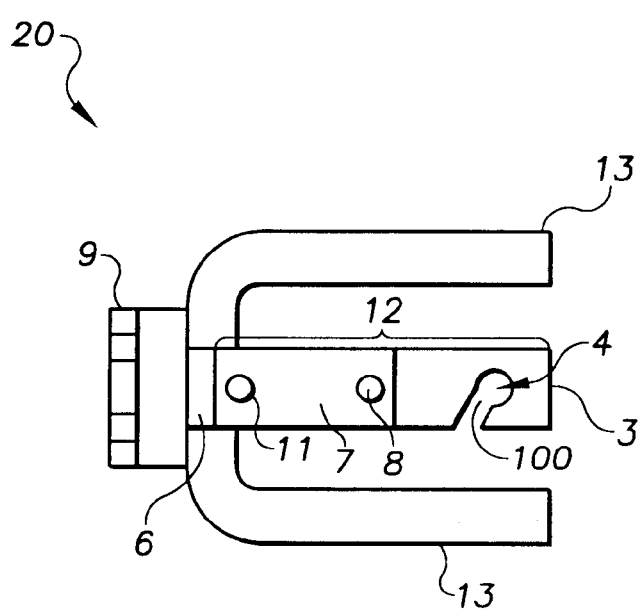
FIG. 3 shows a plan view of one embodiment of the appliance of the present invention.

The resting section (2) has an open center to facilitate an unobstructed access to the root canal by the files. The resting section (2) also has two arms (13), which fix the appliance (20) in the vertical plane by resting on the occlusal surface of the tooth. An elevated central portion (6) of the resting section (2) connects the two arms (13). The elevated central portion (6) extends vertically upwards, perpendicular to the arms, and has a horizontal flat surface at its top. As shown in FIG. 3, the arms (13) preferably form a C shape when viewed from above.

The guide section (12) of the appliance (20) is parallel to the resting section (2) and preferably lies a few millimeters above it. The guide section (12) is preferably manufactured to pivot when used for molars, but is fixed when used for premolars, canines, or incisors. The guide section (12) includes two elongated sections (3) and (7) that are connected at one end. Each of the elongated sections (3) and (7) preferably contains two holes. In FIGS. 1 and 3, one hole on each elongated section (3) and (7) lines up and is used to connect the two elongated sections (3) and (7) with a first connector (8). The other end of section (7) is connected to the horizontal surface of the elevated portion (6) of the resting section (2) with a second connector (11). For a pivoting guide section (12), the connectors (8) and (11) are preferably a hinge, a ball and socket joint, or any other connector capable of allowing movement of the guide section (12). For a fixed guide section (12), the connectors (8) and (11) are preferably nuts and bolts, screws, or nails, but any fastener which fixes the sections together could be used. By utilizing connectors (8) and (11) to connect the guide section (12) to the rest of the appliance (20), the guide section (12) is disconnectable from the remainder of the appliance (20). The guide section (12) can be independently cleaned or sterilized, or is alternatively disposable. The hole (4) at the other end of section (3) is left free unattached and moveable. It is through this free hole (4) that files are preferably placed and abutted. With this arrangement, the files can be moved about horizontally and vertically but only to the limit of the working length of the root canal that is measured and recorded. In a preferred embodiment, there is a slot (100) on the side of the hole (4) to facilitate the placement of the file into the appliance (20) from the side. By inserting a file in this slot (100), the appliance (20) maintains better sterility than prior art devices.

In this embodiment, however, there are only two pieces of the appliance (25) to manufacture. Each of these pieces are preferably cut or formed from a single sheet of material. Alternatively, they are manufactured separately. The first, largest piece includes the attachment section (14) and the resting section (15). Part of the attachment section (14) is formed into a triangular section (21). The triangular section (21) is preferably formed by bending a flat piece of the material. Once this piece is initially formed, only one hole needs to be placed in this piece of the material. One additional piece, an elongated section (17), makes up the guide section (16), and is preferably also cut or formed from the material. Two holes are placed in the elongated section (17). Instead of a guide section (16) with two connectors and three pieces that was seen in the first embodiment, this embodiment has only one connector and two pieces. Alternatively, if the guide section (16) was fixed, the guide section (16) could just extend from the elevated central portion (26) of the resting section (15) and there would be no need for connectors (see FIGS. 15–16). One end of the elongated section (17) is connected to the elevated central portion (26) of the resting section (15) (see FIG. 5) of the first piece of the appliance (25). The other end of the elongated section (17), which is free, contains a hole (18) to preferably move to cover all the area enclosed within the arms (23) of the resting section (15).

The attachment section (14) utilizes a matrix retainer and band, and is preferably U-shaped in cross section (see FIG. 5). Instead of the two grooves (5) shown in FIGS. 1–4, in this embodiment there is a section (21) triangular in cross-section that fits into the triangular area that is formed between the tooth and the matrix band during use. The shape of the triangular section (21) facilitates or ensures more surface area for the matrix band to apply pressure unto the appliance to ensure it is rigidly attached to the tooth during use. An arm (22) of the attachment section (14) is a continuation of the rest of the appliance (25).

Figure 7:
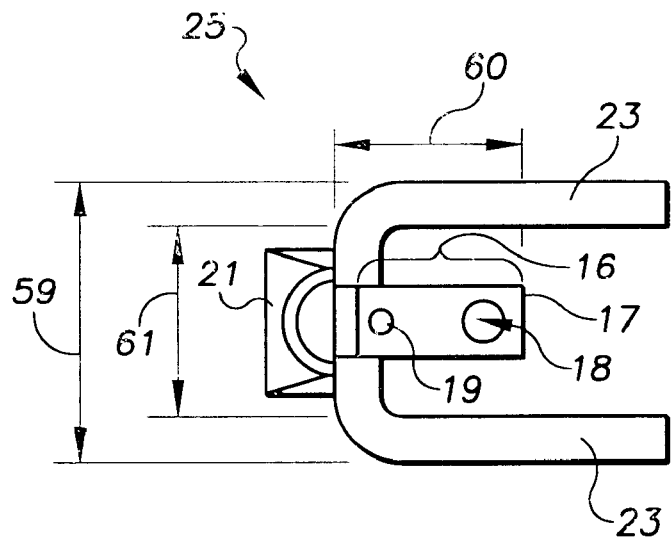
FIG. 7 shows a plan view of a second embodiment of the appliance of the present invention.
Figure 8:
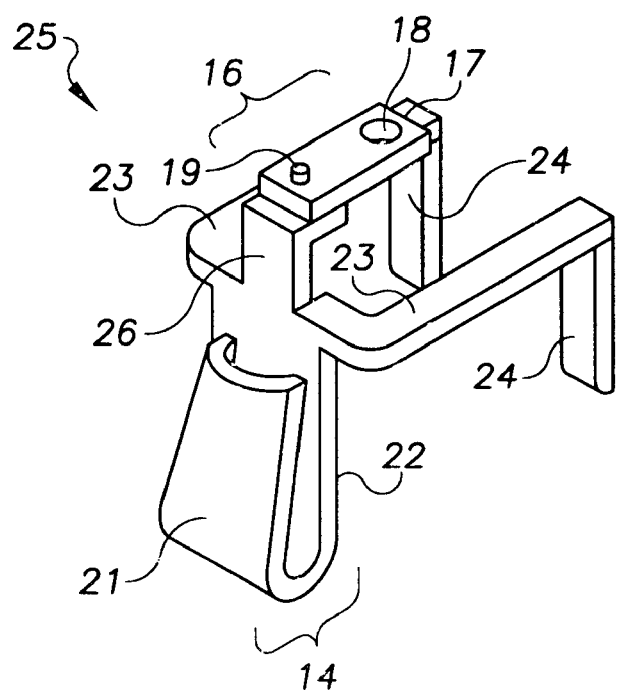
FIG. 8 shows an isometric view of a second embodiment of the appliance of the present invention.
Figure 9:
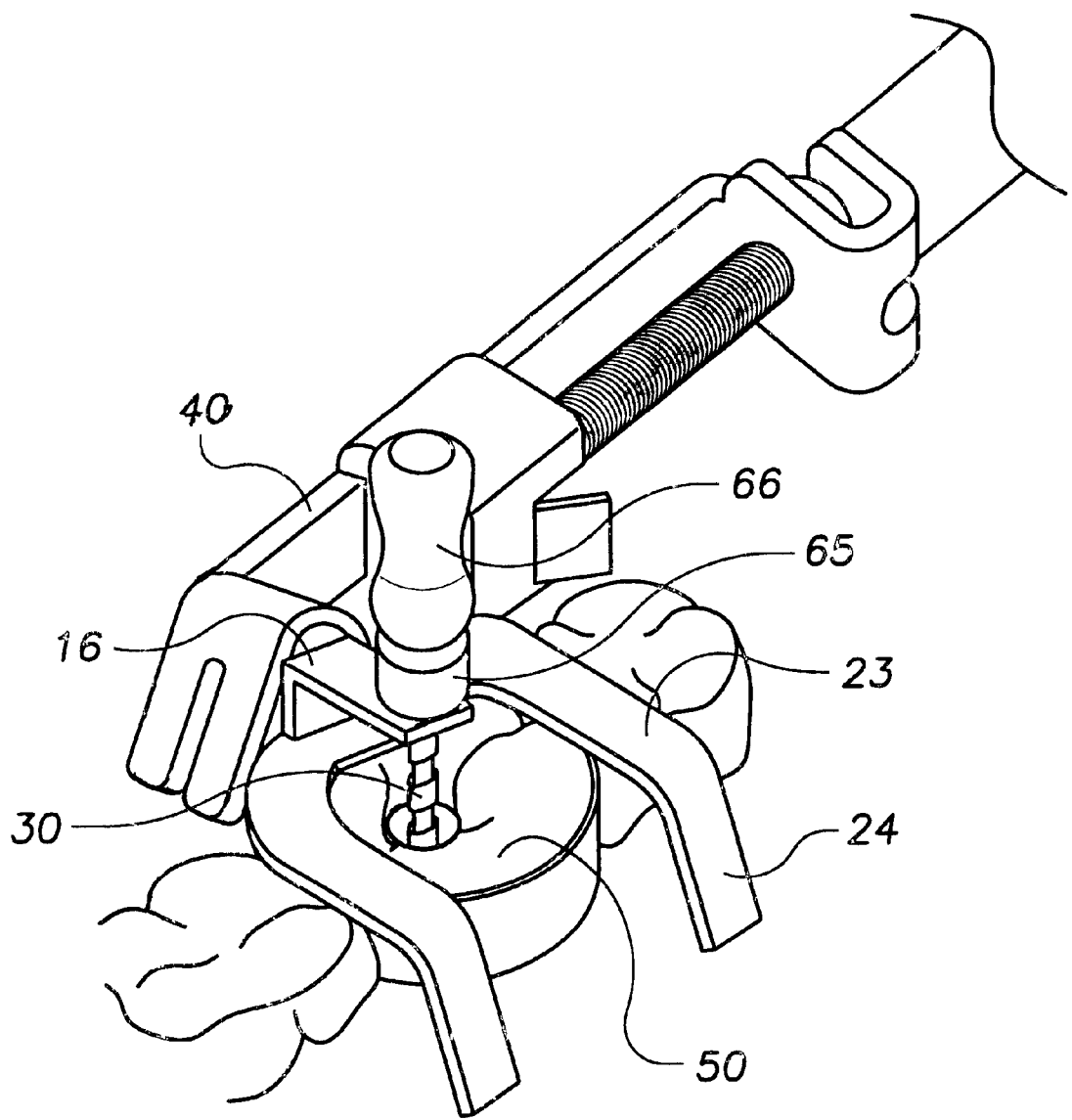
FIG. 9 shows a close-up lingual view of the appliance on a molar in the second embodiment of the present invention.
Figure 10:
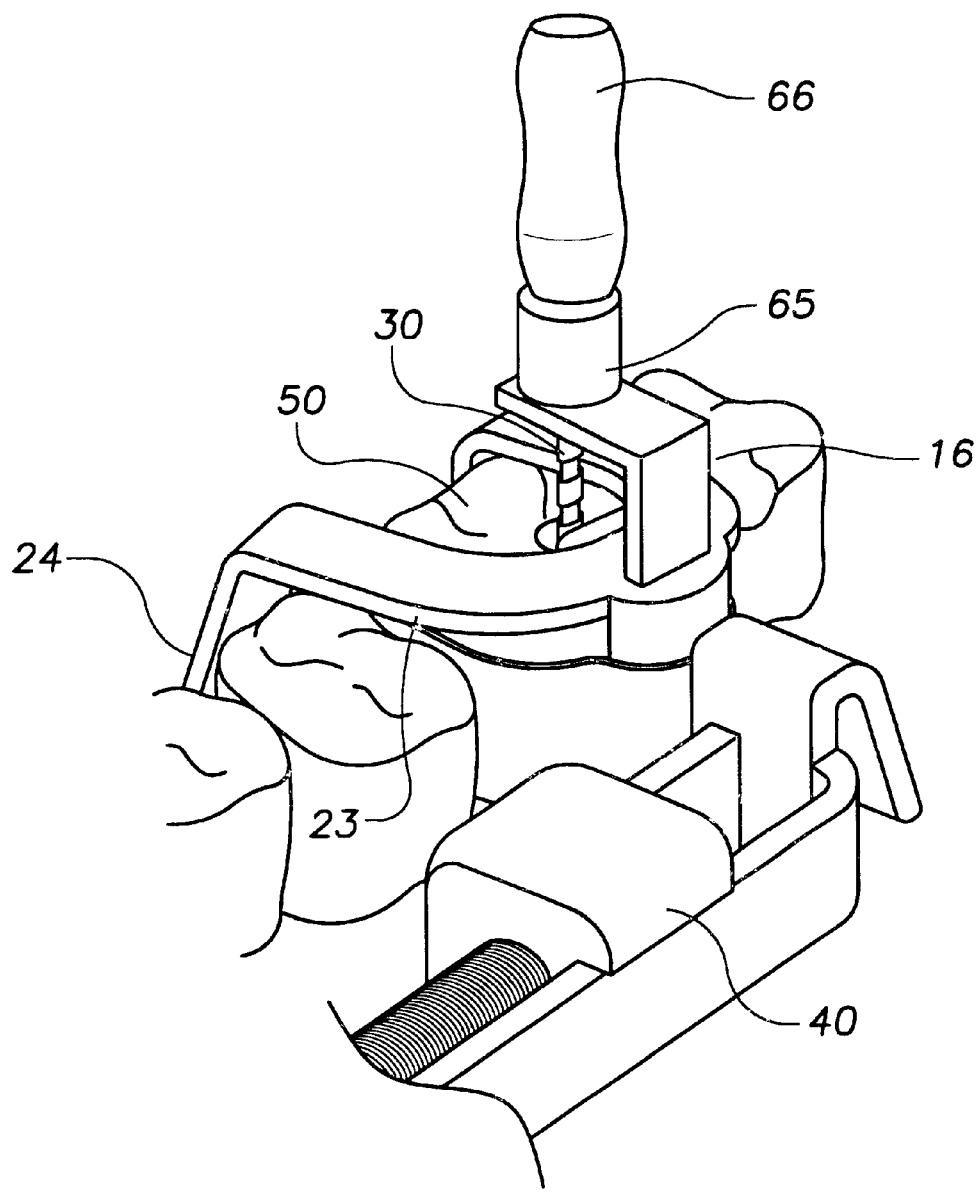
FIG. 10 shows a close-up buccal view of the appliance on a molar in the second embodiment of the present invention.
Figure 11:
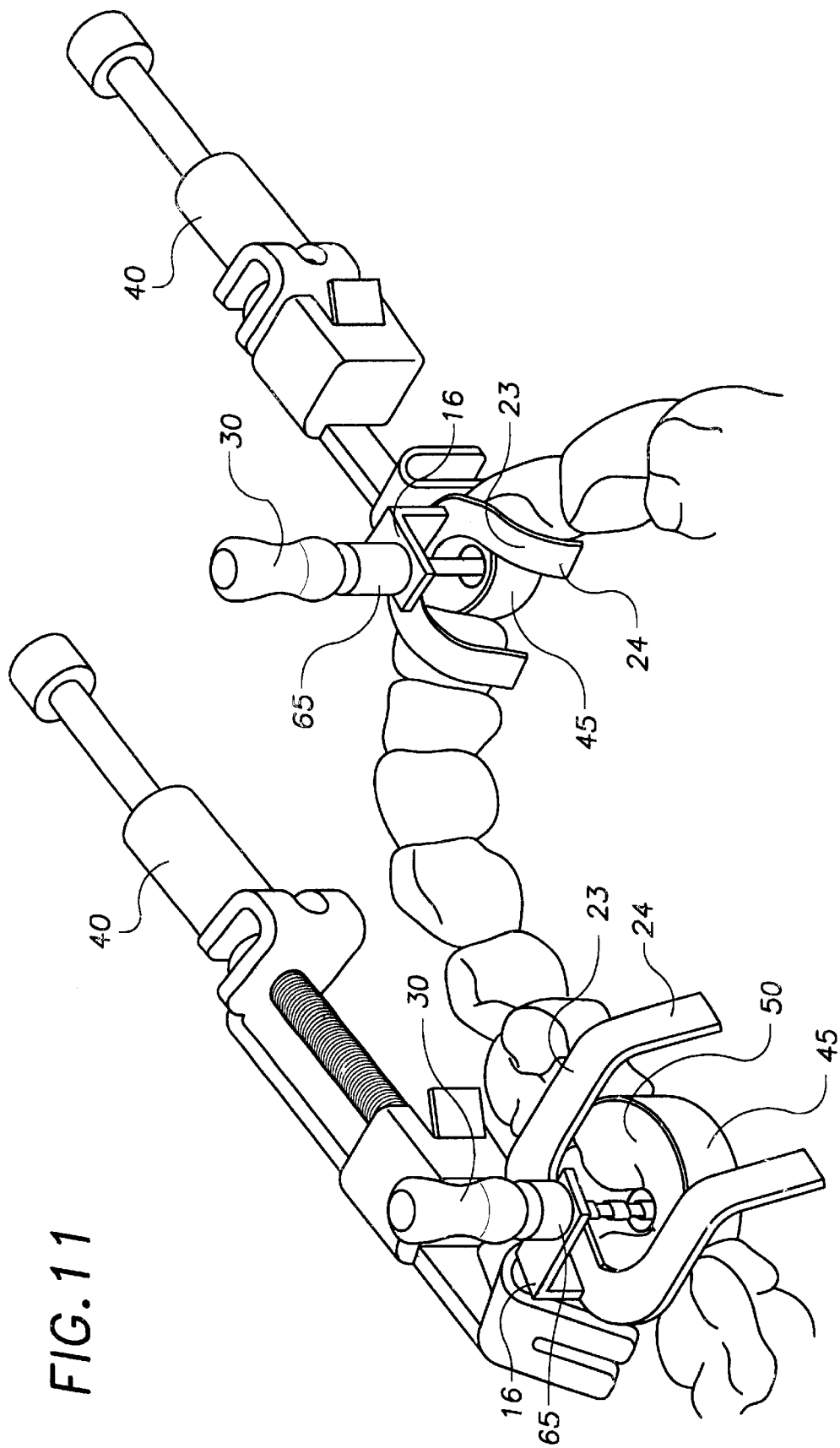
FIG. 11 shows a view of two appliances of the present invention on a set of teeth.
Figure 12:
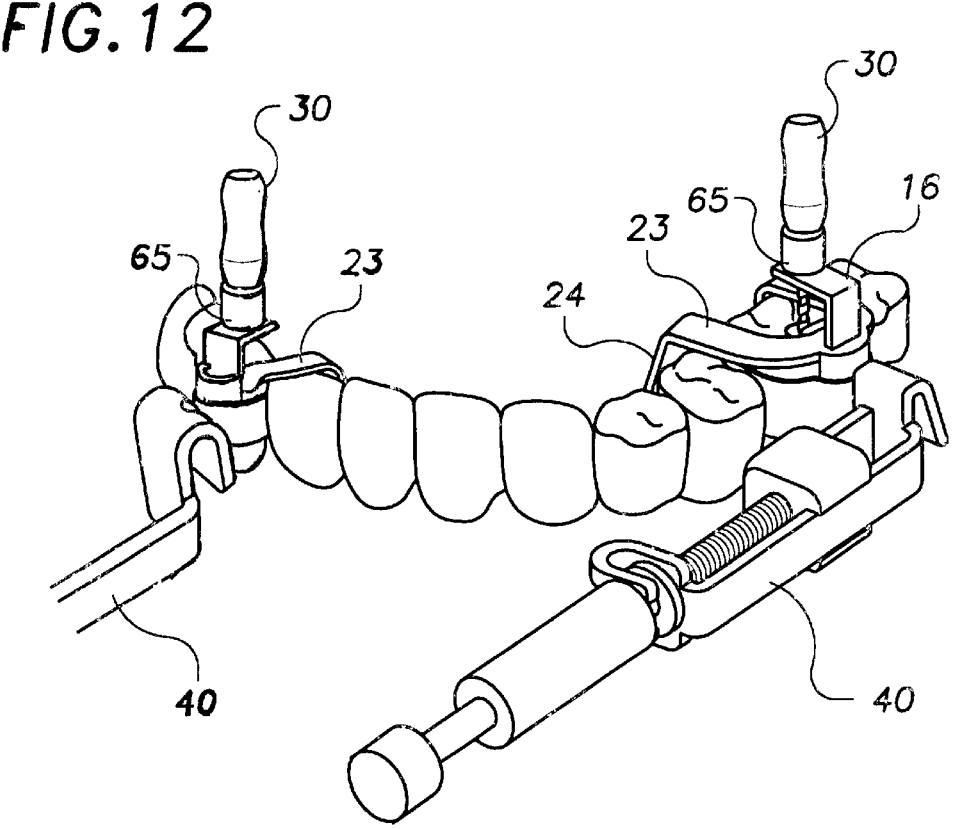
FIG. 12 shows another view of two appliances of the present invention on a set of teeth shown in FIG. 11.
Figure 13:
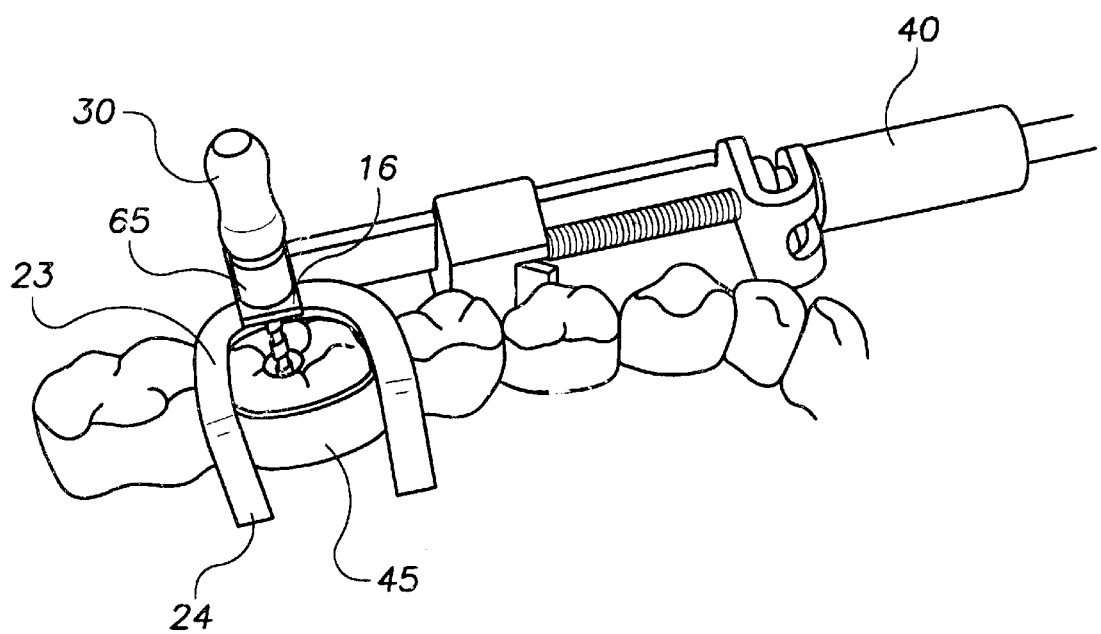
FIG. 13 shows a close-up view of two appliances of the present invention on a set of teeth shown in FIG. 11.

The resting section (15) has an open center to facilitate an unobstructed access to the root canal by the files. The resting section (15) also has two arms (23) which fix the appliance (25) in the vertical plane by resting on the occlusal surface of the tooth. An elevated central portion (26) of the resting section (15) connects the two arms (23). The elevated central portion (26) extends vertically upwards, perpendicular to the arms (23), and has a horizontal flat surface at its top. As shown in FIG. 7, the arms (23) preferably form a C shape when viewed from above.

There are also two extensions (24) attached to the free ends of the arms (23), which run perpendicular to the arms (23). The appliance preferably functions like a rubber dam clamp. The buccal section of the appliance, the attachment section (14), replaces the buccal wing of the clamp and the lingual section, or the extensions (24), function as the lingual wing of the clamp. There is insufficient space in the mouth to use a dental dam clamp here, so the extensions (24) and the attachment section (14) effectively substitute for one.

The guide section (16) of the appliance (25) is parallel to the resting section (15) and preferably lies a few millimeters above it. The guide section (16) is preferably manufactured to pivot when used for molars, but is fixed when used for premolars, canines, or incisors. The guide section (16) includes one elongated section (17) that is connected to the horizontal surface of the elevated central portion (26) of the resting section (15) at one end with a connector (19). For a pivoting guide section (16), the connector (19) is preferably a hinge, a ball and socket joint, or any other connector capable of allowing movement of the guide section (16). For a fixed guide section (16), the connector (19) is preferably nuts and bolts, screws, or nails, but any fastener which fixes the sections together could be used. The elongated section (17) preferably has one hole for the connection to the elevated central portion (26) and a second hole for insertion of a file during use. The hole (18) is left free unattached and moveable. It is through this free hole (18) that the files are preferably placed and abutted. With this arrangement, the files can be moved about horizontally and vertically but only to the limit of the working length of the root canal that is measured and recorded. By utilizing a connecting mechanism to connect the guide section (16) to the rest of the appliance (25), the guide section (16) is disconnectable from the remainder of the appliance (25). The guide section (16) can be independently cleaned or sterilized, or is alternatively disposable. In a preferred embodiment, there is a slot (100) on the side of the hole (18) to allow the file to be placed into the appliance (25) from the side. By inserting a file in this slot (100), the appliance (25) maintains better sterility than prior art devices.

In a preferred embodiment of the appliance (25) shown in FIGS. 5–8, features of the appliance have the following dimensions, indicated by the reference numerals on FIGS. 5–7. In FIG. 5, the preferred dimensions shown are 3 mm (51), 8 mm (52), 10 mm (53), 12 mm (54), and 1 mm (55).

In FIG. 6, the preferred dimensions shown are 1 mm (55), 2.5 mm (56), 2 mm (57), 5 mm (58), and 14 mm (59). FIG. 7 shows 5 mm (60), 10 mm (61), and 14 mm (59) preferred dimensions.

It will be understood that features of these two embodiments are merely examples of the appliance of the invention, and that adapting the invention to combine or swap any of the features is within the ability of one skilled in the art.

In an alternative embodiment, if the tooth to be treated is badly broken down and the appliance (20) or (25) cannot be attached ot it, the appliance (20) or (25) can be attached to an adjacent tooth. The guide section (12) or (16) is modified by elongation. With this modification, the guide section (12) or (16) is able to extend over the tooth in question and the appliance (20) or (25) successfully provides a fixed platform over the tooth.

Referring to FIGS. 9 through 13, the appliance (25) as described in the second embodiment is being used on a molar (50), in conjunction with a matrix band (45), matrix retainer (40) and a file (30). As can be seen in the FIGS., the arms (23) of the appliance (25) rest on the occlusal surface of the tooth and fix the appliance (25) in the vertical plane. The extensions (24) extend over to the lingual side of the tooth (50). The matrix band (45) and matrix retainer (40) fix the appliance (25) in the mouth by attaching to the triangular section (21) of the appliance (25). The triangular section (21) (not shown, see FIGS. 5–8) fits into the triangular area formed between the tooth (50) and the matrix band (45). Alternatively, as shown in the first embodiment, the appliance (20) is attached to the matrix band (45) and matrix retainer (40) using the grooves (5) in the attachment section (1) (not shown, see FIGS. 1–4). The hole (14) found in the guide section (16) is filled with a file (30), which is kept from going beyond the working length due to the fixed platform the appliance (25) creates. A hard stop (65), preferably a rubber stopper, keeps the file (30) from going past the working length.

The device of the present invention is secured with a matrix retainer (40) and matrix band (45) in the mouth against the tooth to be treated. This ensures its immobility. The matrix retainer (40) and band (45) have to be effective in keeping the appliance firmly attached to the tooth. Any movement depends on the effectiveness of the matrix retainer (40) and band (45).

The appliance (20) or (25) is preferably attached to the tooth by any tofflemiere type matrix retainer (40). The matrix band (45) however should be narrow enough so as not to interfere occlusally with the section of the device that rests on the occlusal surface of the tooth. The appliance has to be firmly attached to the tooth so the band (45) has to be fairly strong. To stop any interference to the device, the band (45) should not project above the occlusal surface of the tooth. The matrix band (45) is preferably approximately 0.003 inch thick, and less than or equal to 3/16 inch wide. With the matrix holders (40) currently available, which are very small indeed and do not have a long handle sticking out, the appliance is unobtrusive and easy to work with. If the central portion causes any obstruction of view during use, then the appliance could be made of a transparent clear hard plastic.

The working length is determined by electronic means or x-ray. The extra section of the shaft of the file above the working length is measured or, conversely the working a length is subtracted from the total length of the shaft of the file and the difference is the length of the stopper that is placed on the shaft. To get the working length, the appliance (20) or (25) is used in conjunction with a file of appropriate length to ensure there is adequate space to put measured hard stops and also reach the root apex. Regular rubber stops are preferably used to mark the working length after obtaining it. The length is noted, the rubber stop removed and then hard measured stops are used that are equal to the difference between length of the instrument and the working length. Only one accurate measurement is done and then there is no avenue for error, since the length of the stops is fixed.

Figure 14:
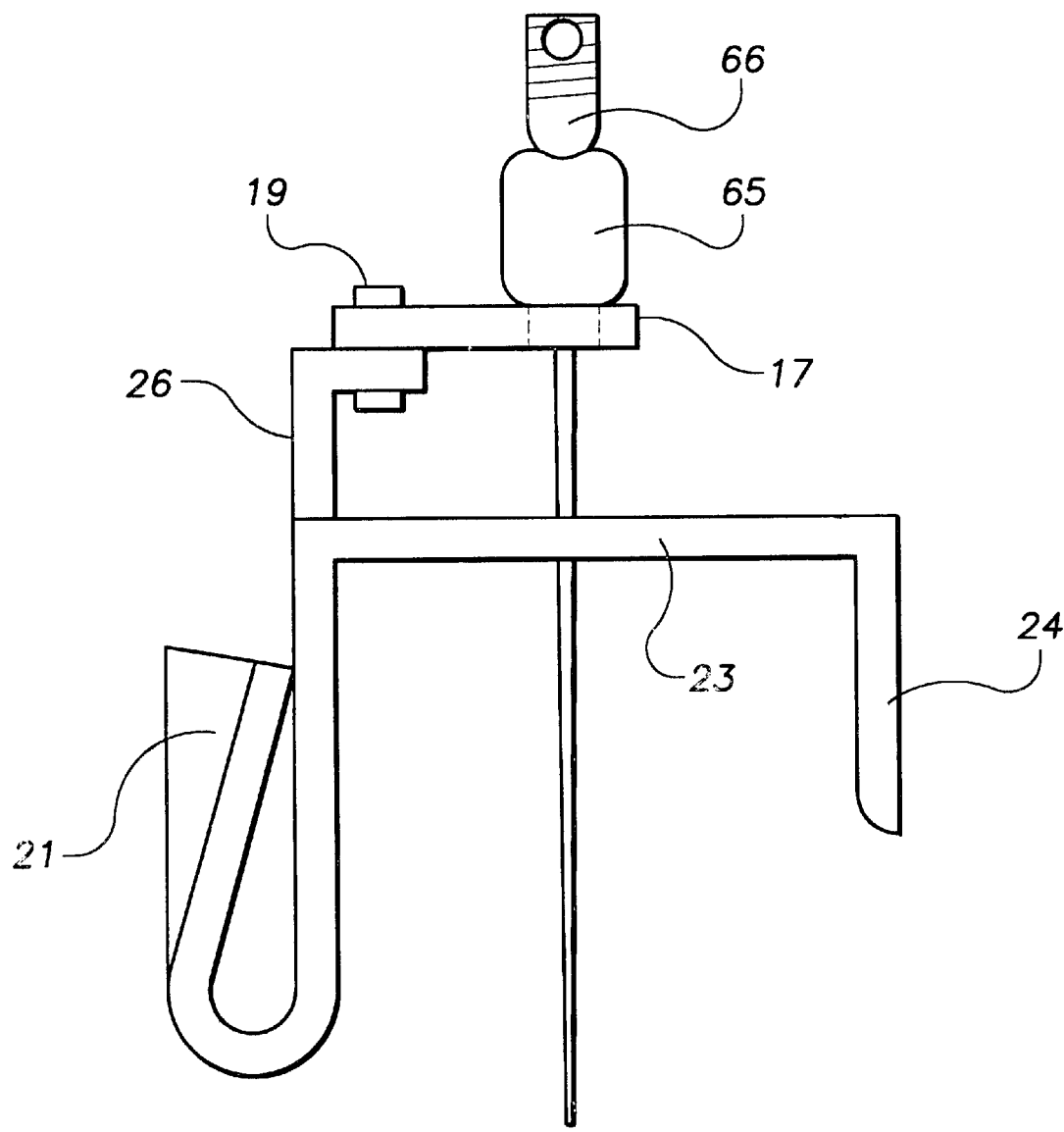
FIG. 14 shows a view of a file inserted into the appliance of the present invention.

Referring also to FIG. 14, in a preferred embodiment, the hard stop (65) occupies all of the space between the bottom of the handle (66) of the file (30) and the guide section (16) of the appliance (25). This placement of the hard stop (65) blocks any further downward movement of the file (30). For each new sterile file (30), a sterile stop (65) is attached with minimal handling to minimize contamination. This ensures that the arms cannot pass further up the instrument. It is against these hard stops (65) that the hole on the guide section (16) abuts. In a preferred embodiment, the hard stops (65) are color-coded for different lengths.

Figure 15:
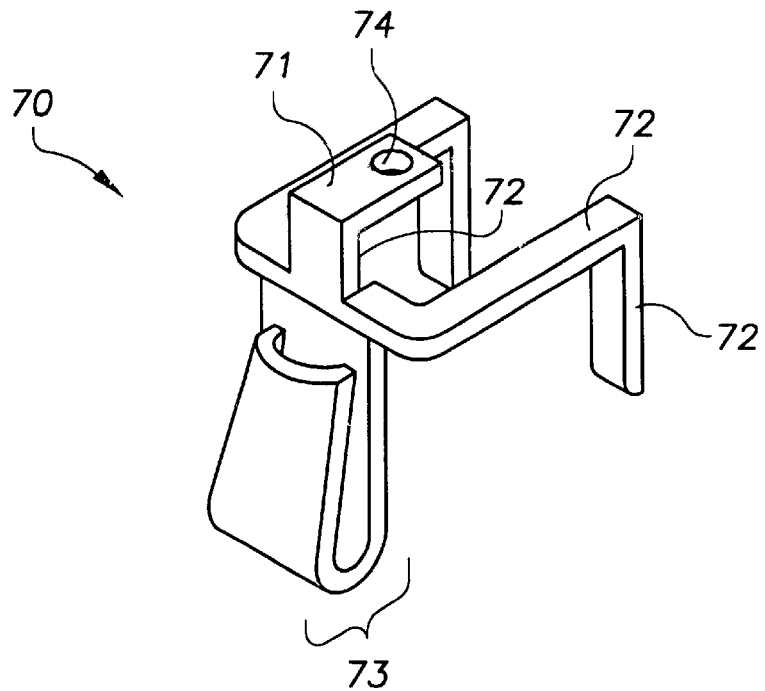
FIG. 15 shows an appliance modified for premolars.
Figure 16:
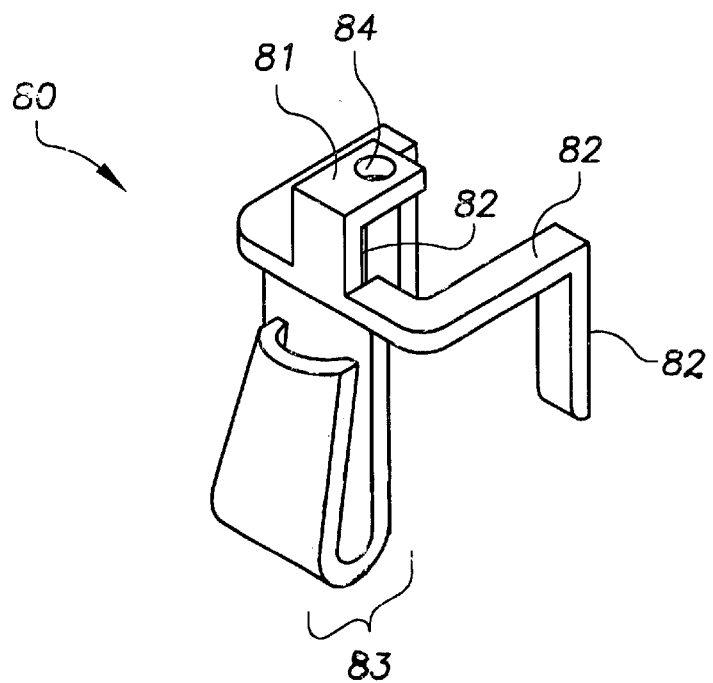
FIG. 16 shows an appliance modified for incisors.

Referring to FIGS. 15 and 16, with only slight variations this device can be used for all the types of teeth in the mouth. There are three preferred tooth-type embodiments of the appliance, which vary according to the type of tooth for which they are made. Each design differs in the guide section. The first appliance is adapted for molars, and shown in FIGS. 1–14. In this variation of the appliance, the guide section is a long pivot section capable of variable movement. A second design adapts the appliance for premolars. The premolar appliance (70) has the same three functional sections as the molar appliance (20) and (25): an attachment section (73), a resting section (72), and a guide section (71) having a hole (74). The guide section (71) in the premolar appliance (70) has a shorter fixed arm which replaces the pivoting section for the molars. There is no connector connecting the resting section (72) to the guide section (71) in this variation of the device. Instead, the guide section (71) is a natural extension of the elevated central portion of the resting section (72). The occlusal, resting section (72) is also preferably made narrower to -match the width of the tooth.

The third adaptation of the appliance is for incisors, which also has an attachment section (83), a resting section (82), and a guide section (81) having a hole (84). In the incisor appliance (80), the guide section (81) is a shorter fixed arm and the whole appliance (80) is narrower mesio-distally to match the width of the tooth. There is no connector connecting the resting section (82) to the guide section (81) in this variation of the device. Similar to the premolar appliance (70), the guide section (81) is a natural extension of the resting section (82). Canine teeth preferably either use the adaptation for the incisors or the premolars, depending upon which is more practical for that specific tooth. For example, some canines are large and would require a premolar type appliance (70), while other canines are smaller and would need an incisor type appliance (80).

In a preferred embodiment, the appliance is used as a kit in combination with known devices. A kit is created depending upon the type of teeth as described above, and also preferably includes additional components. These components include hard stops of varying lengths. These hard stops are preferably color-coded. Standard rubber stops and files are also preferably included in the kit. A matrix band, preferably approximately 0.003 inch thick, and less than or equal to 3/16 inch wide is used in concert with a matrix holder to anchor the appliance.

There are many advantages to using the appliance of the present invention. First, it is ideal for manual use. This device would increase the accuracy of the mechanical and electrical devices discussed in the prior art. Used in conjunction with the present invention, these devices would have a fixed platform on which to work.

Also, the point of reference never changes with the appliance of the present invention. In addition, conventional files can be used with the invention. The stops used are only slightly bigger than conventional stops or, alternatively, a multiple of conventional stops are used to get the required thickness.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A dental appliance to be used in conjunction with an instrument for enlarging a root canal in a tooth, comprising:
   a) an attachment section of the appliance that allows the appliance to be firmly held against the tooth;
   b) a resting section of the appliance comprising at least two arms and a central portion which lies between the arms such that the two arms rest on an occlusal surface of the tooth during use; and
   c) a guide section of the appliance positioned above the tooth comprising:
      i) at least one elongated part connected to the central portion of the resting section wherein the elongated part has a hole for placement of the instrument during an endodontic procedure; and
      ii) a slot adjacent to the hole such that when the instrument is placed into the hole, it can be slid into the hole from a side;
   wherein the appliance acts as a fixed platform from which the instrument has a fixed working length.

2. The appliance of claim 1, wherein the resting section further comprises at least one extension attached to an end of each arm such that the extension begins at the end of the arm and runs perpendicular to the arm.

3. The appliance of claim 1, wherein the arms of the resting section form a C-shape.

4. The appliance of claim 1, wherein the attachment section has a U-shape.

5. The appliance of claim 4, wherein an open end of the U-shape is triangular in shape.

6. The appliance of claim 5, wherein the triangular shape fits into a triangular area formed between the tooth and a matrix band during the endodontic procedure.

7. The appliance of claim 6, wherein a matrix retainer and the matrix band hold the appliance against the tooth.

8. The appliance of claim 4, wherein an open end of the U-shape contains at least one groove.

9. The appliance of claim 8, wherein the grooved end fits into an area formed between the tooth and a matrix band during the endodontic procedure.

10. The appliance of claim 9, wherein a matrix retainer and the matrix band hold the appliance against the tooth.

11. The appliance of claim 1, wherein the guide section comprises two elongated parts connected by a connector selected from the group consisting of a hinge, a nut and bolt, a ball and socket joint, a screw, and a nail.

12. The appliance of claim 1, wherein the instrument is selected from the group consisting of a file and a reamer.

13. The appliance of claim 1, wherein the dental appliance provides an effective stop for the instrument during the endodontic procedure.

14. The appliance of claim 1, wherein the elongated part is fixed.

15. The appliance of claim 14, wherein a type of tooth being worked on is selected from the group consisting of: premolars, canines, and incisors.

16. The appliance of claim 1, wherein the elongated part is capable of pivoting in a horizontal plane during use.

17. The appliance of claim 1, wherein a type of tooth being worked on is a molar.

18. The appliance of claim 1, wherein the resting section is connected to the guide section by a connector selected from the group consisting of: a hinge, a nut and bolt, a ball and socket joint, a screw, and a nail.

19. A kit for controlling a working length of an instrument during a root canal, comprising:
   a) at least one instrument for enlarging the root canal;
   b) an appliance comprising:
      i) an attachment section of the appliance that allows the appliance to be firmly held against the tooth;
      ii) a resting section of the appliance comprising at least two arms and a central portion which lies between the arms such that the two arms rest on an occlusal surface of the tooth during use; and
      iii) a guide section positioned above the tooth comprising at least one elongated part connected to the central portion of the resting section wherein the elongated part has a hole for placement of the instrument during an endodontic procedure;
   wherein the appliance acts as a fixed platform from which the instrument has a fixed working length;
   c) at least one hard stop;
   d) a matrix band;
   e) at least one rubber stopper; and
   f) a matrix holder.

20. The kit of claim 19, wherein the hard stops are color-coded.

21. The kit of claim 19, wherein the instrument is selected from the group consisting of files and reamers.

* * * * *